(12) United States Patent
Couvillon, Jr. et al.

(10) Patent No.: US 7,371,223 B2
(45) Date of Patent: May 13, 2008

(54) ELECTROACTIVE POLYMER ACTUATED HEART-LUNG BYPASS PUMPS

(75) Inventors: Lucien Alfred Couvillon, Jr., Concord, MA (US); Michael S. Banik, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1072 days.

(21) Appl. No.: 10/262,817

(22) Filed: Oct. 2, 2002

(65) Prior Publication Data

US 2004/0068220 A1 Apr. 8, 2004

(51) Int. Cl.
*A61M 37/00* (2006.01)
*A61F 2/08* (2006.01)
*A61N 1/362* (2006.01)
*A61M 1/10* (2006.01)

(52) U.S. Cl. .................. 604/9; 604/6.11; 623/3.12; 623/14.13; 600/16

(58) Field of Classification Search ............. 604/8–10, 604/149, 151, 123, 119, 131–133; 623/1.1, 623/1.12, 1.15, 1.24, 14.13, 3.12, 23.68; 607/2, 9, 103, 106, 116, 119, 127
See application file for complete search history.

(56) References Cited

U.S. PATENT DOCUMENTS

| 4,293,961 A | 10/1981 | Runge .......................... 3/1.7 |
| 4,549,860 A | 10/1985 | Yakich ....................... 417/475 |
| 5,011,469 A | 4/1991 | Buckberg et al. ............... 604/4 |
| 5,250,167 A | 10/1993 | Adolf et al. ................. 204/299 |

(Continued)

FOREIGN PATENT DOCUMENTS

WO   WO 01 06579 A2   1/2001

(Continued)

OTHER PUBLICATIONS

Shahinpoor, M. "Potential applications of electroactive polymer sensors and actuators in MEMS technologies". Proceedings of SPIE. vol. 4234. pp. 203-214. 2001.

(Continued)

*Primary Examiner*—Leslie R. Deak
(74) *Attorney, Agent, or Firm*—Mayer & Williams PC; David B. Bonham, Esq.; Keum J. Park, Esq.

(57) ABSTRACT

A pump apparatus, which comprises: (a) a tubular portion comprising an electroactive polymer actuator that expands and contracts an inner volume of the tubular portion based upon received control signals; and (b) a control unit electrically coupled to the electroactive polymer actuator and sending control signals to the actuator. The pump apparatus can further include at least one valve that is in fluid communication with the inner volume of the tubular portion. The pump apparatus can be used, for example, as a heart-lung bypass pump apparatus. Also disclosed herein is a method of providing circulatory support for patient. The method comprises (a) providing the above pump apparatus; (b) placing an inlet of the pump apparatus in fluid communication with the venous side of the patient's vascular system; (c) placing an outlet of the pump apparatus in fluid communication with the arterial side of the patient's vascular system; and (d) sending control signals to the electroactive polymer actuator thereby pumping blood from the venous side to the arterial side of said patient's vascular system.

32 Claims, 9 Drawing Sheets

U.S. PATENT DOCUMENTS

| | | | |
|---|---|---|---|
| 5,268,082 A * | 12/1993 | Oguro et al. ............... | 204/282 |
| 5,389,222 A | 2/1995 | Shahinpoor ................. | 204/299 |
| 5,437,601 A | 8/1995 | Runge ........................ | 600/16 |
| 5,556,700 A * | 9/1996 | Kaneto et al. .............. | 428/332 |
| 5,631,040 A | 5/1997 | Takuchi et al. ............. | 427/100 |
| 5,800,138 A | 9/1998 | Merce Vives ............... | 417/374 |
| 5,855,565 A | 1/1999 | Bar-Cohen et al. ......... | 604/104 |
| 5,954,058 A | 9/1999 | Flaherty ..................... | 128/899 |
| 6,001,306 A | 12/1999 | McFall et al. ............... | 422/46 |
| 6,109,852 A | 8/2000 | Shahinpoor et al. .......... | 414/1 |
| 6,249,076 B1 | 6/2001 | Madden et al. ............. | 310/363 |
| 6,394,997 B1 * | 5/2002 | Lemelson ................ | 604/890.1 |
| 6,435,840 B1 | 8/2002 | Sharma et al. .............. | 417/322 |
| 6,514,237 B1 | 2/2003 | Maseda ...................... | 604/533 |
| 6,664,718 B2 * | 12/2003 | Pelrine et al. .............. | 310/330 |
| 6,682,500 B2 * | 1/2004 | Soltanpour et al. ............ | 604/9 |
| 2002/0050769 A1 | 5/2002 | Pelrine et al. .............. | 310/363 |

FOREIGN PATENT DOCUMENTS

WO  WO 01/58973  8/2001

OTHER PUBLICATIONS

David L. Brock, "Review of Artificial Muscle Based on Contractile Polymers," Massachusetts Institute of Technology Artifical Intelligence Laboratory, A.I. Memo No. 1330, Nov. 1991, pp. 1-12.

"Biomedical Applications of Electroactive Polymers", http://www.hmc.psu.edu/artorg/electrop/,last update Jan. 15, 2002, pp. 1-3.

Edwin W.H. Jager et al., "Microfabricating Conjugated polymer Actuators," Science, vol. 290, Nov. 24, 2000, pp. 1540-1545.

Ron Pelrine et al., "Applications of Dielectric Elastomer Acuators," Smart Structures and Materials 2001: Electroactive Polymer Actuators and Devices, Proceedings of the SPIE, vol. 4329, pp. 335-349.

Yoseph Bar-Cohen, Ed., Electroactive Polymer (EAP)Actuators as Artificial Muscles: Reality, Potential, and Challenges, SPIE Press, 2001, Chapter 1, pp. 3-44.

Yoseph Bar-Cohen, Ed., Electroactive Polymer (EAP) Actuators as Artifical Muscles: Reality, Potential, and Challenges, SPIE Press, 2001, Chapter 7, pp. 193-221.

Yoseph Bar-Cohen, Ed., Electroactive Polymer (EAP) Actuators as Artifical Muscles: Reality, Potential, and Challenges, SPIE Press, 2001, Chapter 16, pp. 457-495.

Yoseph Bar-Cohen, Ed., Electroactive Polymer (EAP) Actuators as Artifical Muscles: Reality, Potential, and Challenges, SPIE Press, 2001, Chapter 21, pp. 615-659.

Yoseph Bar-Cohen, Ed., WorldWide ElectroActive Polymers (Artificial Muscles) Newlsetter, vol. 3, No. 1, (Jun. 2001), pp. 1-14.

John D.W. Madden et al., "Polypyrrole actuators: modeling an performance," Smart Structures and Materials 2001: Electroactive Polymer Actuators and Devices, Proceedings of the SPIE, vol. 4329, pp. 72-83.

Yoseph Bar-Cohen, "Transition of EAP material from novelty to practical applications—are we there yet?," Smart Structures and Materials, 2001: Electroactive Polymer Actuators and Devices, Proceedings of the SPIE, vol. 4329, pp. 1-6.

Nakhiah Goulbourne, "Engineering Design & Optimization group," http://edog.me.psu.edu/students/nakhiah.goulbourne.html, last updated Aug. 26, 2000, 1 page.

Philip N. Cascade, M.D., "Cardiopulmonary Support Devices," http://www.thoracicrad.org/STR_Archive/PostgraduatePapers/CascadePN.html, pp. 1-7.

* cited by examiner

ELECTROACTIVE POLYMER ACTUATED HEART-LUNG BYPASS PUMPS

FIELD OF THE INVENTION

The present invention relates to heart-lung bypass pumps and more particularly to heart-lung bypass pumps that are driven by electroactive-polymer based actuators.

BACKGROUND OF THE INVENTION

Bypass pumps are put into medical use in instances where a patient requires circulatory support. For example, bypass pumps are widely used in heart surgery to support blood flow while the surgeon repairs heart chambers, heart valves, coronary vessels and so forth. Coronary artery bypass grafting (CABG) is a common example of such surgery.

During a typical bypass surgical procedure, cannulas/catheters inserted into the patient's venous and arterial circulations are connected via tubing sets to an oxygenator and pump console. The pump console is typically based upon a roller-type pump. Unfortunately, roller type pumps suffer from a number of disadvantages, for example: (a) the squeezing of the tubing in the roller causes hemolysis, which is detrimental to the patient, (b) setup and sterilization of the complex pump-tubing-oxygenator system, and particularly of the roller-type pump, is time-consuming and expensive, typically involving specialized operating room perfusionist staff, (c) roller pump consoles are big, occupying a large amount of space in an already crowded operating room, (d) the priming volume of roller-pump systems is large; (e) priming with saline causes hemodilution and anemia, while priming with blood involves the risks that are attendant with transfusion, and (f) unlike the heart, roller pumps deliver a pulseless flow.

Many or the above and other disadvantages of the prior art are addressed by the bypass pumps of the present invention.

SUMMARY OF THE INVENTION

The present invention is directed to novel bypass pumps in which flow is achieved using one or more electroactive polymer actuators.

According to an embodiment of the present invention, a pump apparatus is provided which comprises: (a) a tubular portion including an electroactive polymer actuator that expands and contracts an inner volume of the tubular portion based upon received control signals; and (b) a control unit electrically coupled to the electroactive polymer actuator and sending the control signals to the actuator. The pump apparatus of the present invention can be, for example, a bypass pump apparatus.

In some embodiments, the pump apparatus of the present invention further includes at least one valve that is in fluid communication with the inner volume of the tubular portion. For example, the pump apparatus can further include first and second valves in fluid communication with the inner volume of the tubular portion, in which the first valve is disposed between the tubular portion and an inlet of the pump apparatus and in which the second valve is disposed between the tubular portion and an outlet of the pump apparatus. The first valve typically allows increased fluid flow when the inner volume is expanded and decreased fluid flow when the inner volume is contracted, while the second valve allows increased fluid flow when the inner volume is contracted and decreased fluid flow when the inner volume is expanded. Valves having such fluid flow characteristics include check valves and control valves.

In some embodiments, the tubular portion will comprise two or more of the electroactive polymer actuators.

In some embodiments, the pump apparatus will comprise a plurality of tubular portions. In certain embodiments, the pump apparatus will comprise n tubular portions and n+1 valves, where n is an integer greater than or equal to 1.

To provide the desired expansion and contraction of the inner volume of the tubular portion, the electroactive polymer actuator can be disposed such that it at least partially surrounds (i.e., wraps around) the longitudinal axis of the tubular portion. For example, the electroactive polymer actuator can circumferentially surround the longitudinal axis of the tubular portion (e.g. it can be provided in the form of a band). As another example, the electroactive polymer actuator can surround the longitudinal axis of the tubular portion in the form of a helix.

In some embodiments, the electroactive polymer actuator will comprise an electroactive polymer region, a counter-electrode region, and an electrolyte-containing region disposed between the electroactive polymer region and the counter-electrode region. In certain embodiments, the electroactive polymer actuator is disposed between and inner and outer walls of the tubular portion. For example, the tubular portion can comprise a counter-electrode region, an electrolyte containing region and an electroactive polymer region, all disposed between inner and outer layers, which can be elastomeric polymer layers. The tubular portion also beneficially contains inner and outer passivation layers as well.

According to another embodiment of the present invention, a method of providing circulatory support for a patent is provided. The method comprises (a) providing the above pump apparatus; (b) placing the inlet of the pump apparatus in fluid communication with the venous side of the patient's vascular system; (c) placing the outlet of the pump apparatus in fluid communication with the arterial side of the patient's vascular system; and (d) sending the control signals to the electroactive polymer actuator thereby pumping blood from the venous side to the arterial side of the patient's vascular system.

In some embodiments, the control signals will be in the form of a wave having predetermined characteristics, for example, a characteristic frequency and amplitude. For example, the characteristics of the wave (e.g., the frequency, the amplitude, or both) can be set by a human operator or can be determined by a computer program, for example, based on at least one physiological patient sensor input.

In some embodiments, the control signals will sequentially actuate a series of electroactive polymer actuators such that a region of contracted inner volume is advanced along the longitudinal length of the tubular portion.

One advantage of the bypass pumps of the present invention is that a pumping system can be provided, which has a significantly lower priming volume than prior art pumping systems that are based on roller pumps. For example, because the pump can be configured as an in-line tube, the tubing ends can be directly connected to the input (e.g., venous) and exit (e.g., arterial) vessels, creating a minimally invasive, low volume, temporary bypass device. Moreover, priming volume in the bypass pumps of the present invention can be further reduced by priming the tubing system in its constricted state.

Another advantage of the bypass pumps of the present invention is that hemolysis is typically low, because there is little or no squeezing damage to blood cells as in prior art prior art roller pump systems.

Yet another advantage of the bypass pumps of the present invention is their potential for low cost. Because the bypass pumps of the present invention are relatively simple, they can be manufactured at relatively low cost, allowing them to be provided in a pre-assembled, sealed, "plug-and-play" format, ready for use in the operating room with minimum inventory and storage space.

Moreover, the bypass pumps of the present invention can free up space that is normally occupied next to the operating table by a roller pump, console. For example, due to their small size, the bypass pumps of the present invention can be hung, along with an oxygenator, from an IV stand upon or next to the operating table.

Yet another advantage of the bypass pumps of the present invention is their ability to provide pulsed output, which can be tailored to appropriate physiologic conditions associated with the systole and diastole of the heart.

These and other embodiments and advantages of the present invention will become apparent from the following detailed description, and the accompanying drawings, which illustrate by way of example the features of the invention.

DETAILED DESCRIPTION OF THE INVENTION

The present invention now will be described more fully hereinafter with reference to the accompanying drawings, in which several embodiments of the present invention are shown. This invention may, however, be embodied in different forms and should not be construed as limited to the embodiments set forth herein.

According to an embodiment of the present invention, a bypass pump is provided, which is made from tubing that constricts and expands based on electronic control of one or more electroactive polymer actuators. Although various bypass pumps are described in detail herein, the pumps of the present invention are also useful for other applications in which a sealed system is desired, besides bypass applications. Movement of hazardous materials is one specific example.

Actuators based on electroactive polymers are preferred for the practice of the present invention, for example, due to their small size, large force and strain, low cost and ease of integration into the infusion pumps of the present invention.

Electroactive polymers, members of the family of plastics referred to as "conducting polymers," are a class of polymers characterized by their ability to change shape in response to electrical stimulation. They typically structurally feature a conjugated backbone and have the ability to increase electrical conductivity under oxidation or reduction. Some common electroactive polymers are polyaniline, polysulfone, polypyrrole and polyacetylene. Polypyrrole is pictured below:

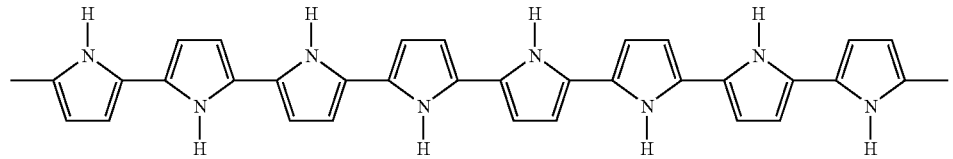

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium that is coupled to the polymer surface. The electrolyte may be, for example, a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, expansion is due to ion insertion between chains, whereas in others inter-chain repulsion is the dominant effect. Regardless of the mechanism, the mass transfer of ions into and out of the material leads to an expansion or contraction of the polymer.

Currently, linear and volumetric dimensional changes on the order of 25% are possible. The stress arising from the dimensional change can be on the order of 3 MPa, far exceeding that exerted by smooth muscle cells, allowing substantial forces to be exerted by actuators having very small cross-sections. These characteristics are ideal for construction of the bypass pumps of the present invention.

Figure 1:
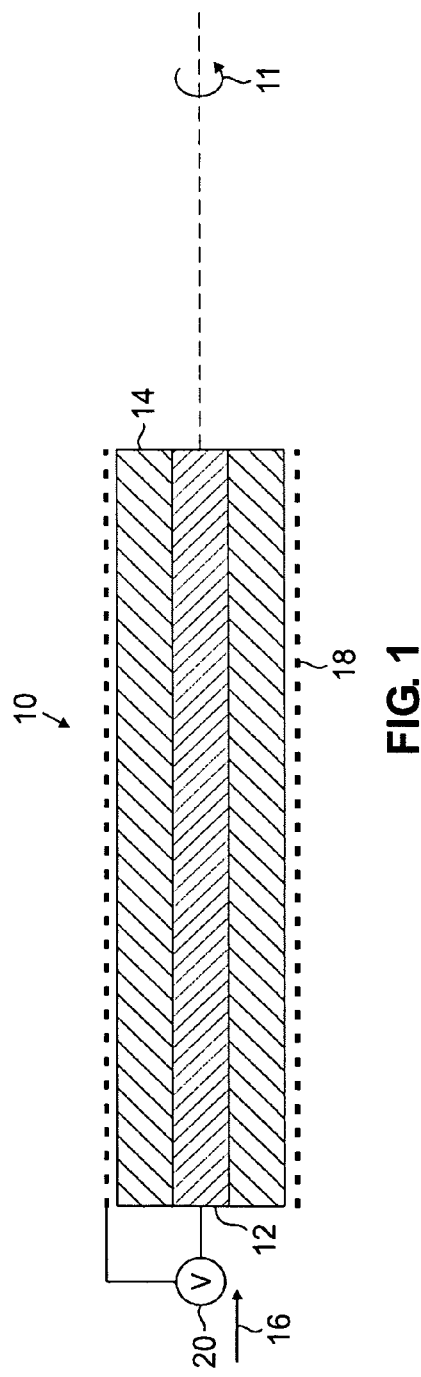
FIG. 1 is a schematic cross-sectional view of a prior art electroactive polymer actuator useful in connection with certain embodiments of the present invention.

Referring now to FIG. 1, taken from U.S. Pat. No. 6,249,076, an electroactive polymer actuator 10 is shown schematically in cross-section. Active member 12 of actuator 10 has a surface coupled with electrolyte 14 and has a longitudinal axis 11. Active member 12 includes an electroactive polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media.

Many geometries are available for the relative disposition of member 12 and electrolyte 14. In accordance with some embodiments of the invention, member 12 may be a film, a fiber, a group of fibers, or a combination of multiple films and fibers disposed so as to act collectively to apply a tensile force in a longitudinal direction substantially along axis 11 in this instance. The fibers may be bundled or distributed within the electrolyte 14.

Active member 12 includes an electroactive polymer. Many electroactive polymers having desirable tensile properties are known to persons of ordinary skill in the art. In accordance with some embodiments of the invention, active member 12 can be a polypyrrole film. Such a polypyrrole film may be synthesized, for example, by electrodeposition according to the method described by M. Yamaura et al., "Enhancement of Electrical Conductivity of Polypyrrole Film by Stretching: Counter-on Effect," Synthetic Metals, vol. 36, pp. 209-224 (1988), which is incorporated herein by reference. In addition to polypyrrole, any conducting polymer that exhibits contractile or expansile properties may be used within the scope of the invention. Polyaniline, polysulfone, polyacetylene are examples.

Electrolyte 14 may be, for example, a liquid, a gel, or a solid, so long as ion movement is allowed. Moreover, where the electrolyte 14 is a solid, it will typically move with the active member 12 and will typically not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution, KCl, NaCl and so forth. The electrolyte may be non-toxic in the event that a leak inadvertently occurs in vivo.

Counter electrode 18 is in electrical contact with electrolyte 14 in order to provide a return path for charge to a source 20 of potential difference between member 12 and electrolyte 14. Counter electrode 18 may be any suitable electrical conductor, for example, another conducting polymer, a conducting polymer gel, or a metal such as gold or platinum. Counter electrode 18 can be, for example, in wire or film form and can be applied, for example, by electroplating, chemical deposition, or printing. In order to activate actuator 10, a current is passed between active member 12 and counter electrode 18, inducing contraction or expansion of member 12. Additionally, the actuator may have a flexible skin for separating the electrolyte from an ambient environment.

The actuators can be provided in an essentially infinite array of configurations as desired, including planar actuator configurations (e.g., with planar active members and counter-electrodes), cylindrical actuator configurations (e.g., see the actuator illustrated in FIG. 1, which is illustrated as having a cylindrical active member and wire coil counter electrode), and so forth.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72-83), both of which are hereby incorporated by reference in their entirety.

Figure 2A:
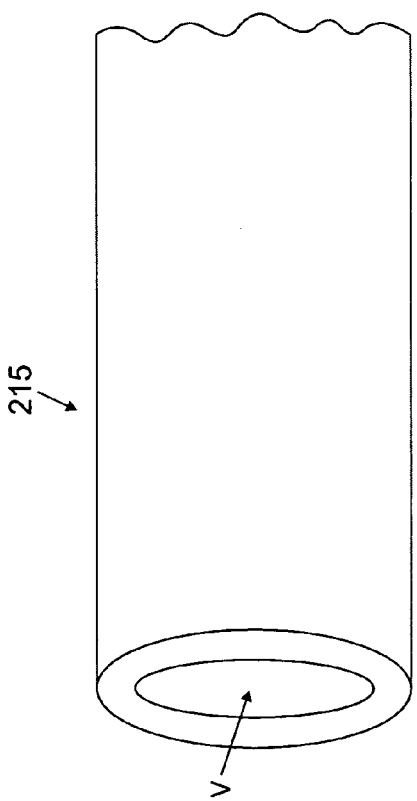
FIGS. 2A and 2B are partial, schematic, perspective views illustrating the expansion and contraction of an interior volume of a tubular portion of a bypass pump, according to an embodiment of the present invention.
Figure 2B:
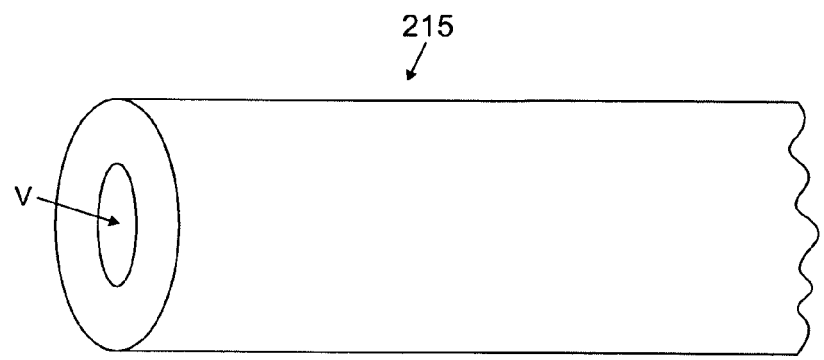

In some embodiments, the bypass pumps of the present invention contain at least one tubular portion, which has an inner volume that is expanded and contracted using one or more electroactive polymer actuators. FIGS. 2A and 2B illustrate partial schematic views of a tubular portion 215 in expanded and contracted states in accordance with an embodiment of the present invention. By providing one or more electroactive polymer actuators (not shown) upon or within the wall of the tubular portion, the inner volume of the tubular member V can be contracted or expanded upon application of appropriate control signals from a control unit (not shown). Typically, the inner volume of the tubular member V is contracted upon contraction of the actuators(s), while the inner volume of the tubular member V is expanded upon expansion of the actuators(s). As discussed in more detail below, in addition to one or more tubular portions 215, the bypass pumps of the present invention can also be provided with one or more valves to reduce backflow.

Figure 8A:
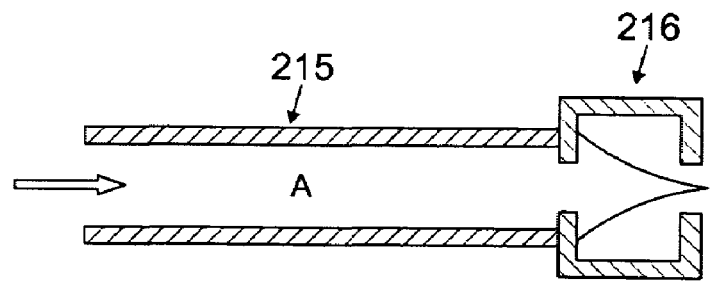
FIGS. 8A and 8B are partial, schematic, cross-sectional views illustrating the operation of a bypass pump in accordance with an embodiment of the present invention.
Figure 8B:
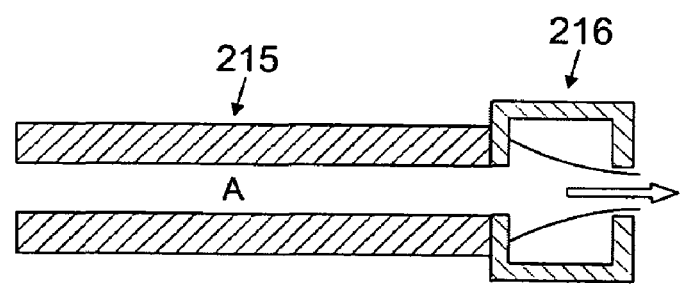

Advancement of fluid through a bypass pump in accordance with one embodiment of the present invention is illustrated in FIGS. 8A and 8B. In FIG. 8A, a control signal is sent to one or more electroactive polymer actuators (not shown) within tubular portion 215 such that chamber A (which corresponds to the internal volume of tubular portion 215) is expanded. Due to the directional orientation of check valve 216 in FIG. 8A (which is schematically illustrated as a duckbill check valve), no fluid flow occurs from the right through the check valve into chamber A. Instead, fluid can only flow from the left to as indicated by the arrow in FIG. 8A. Upon contraction of chamber A as illustrated in FIG. 8B, on the other hand, fluid does flow from left to right through the check valve. Although no check valve is provided to the left of tubular portion 215, due to the presence of check valve 216, the net fluid flow over multiple expansion and contraction cycles will be will be to the right.

Figure 3A:
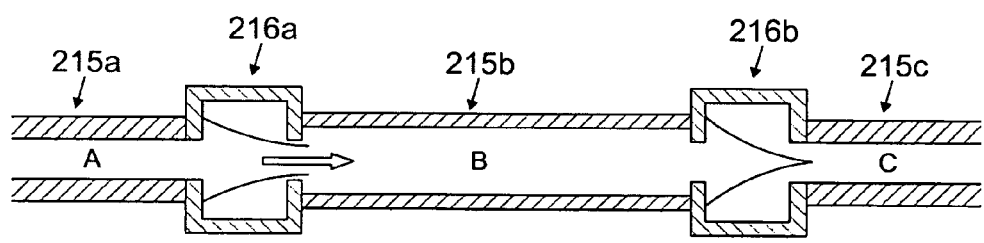
FIGS. 3A and 3B are partial, schematic, cross-sectional views illustrating the operation of a bypass pump in accordance with an embodiment of the present invention.
Figure 3B:
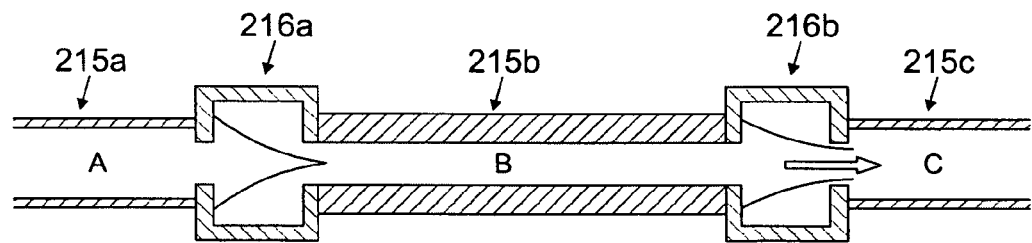

Advancement of fluid through a bypass pump in accordance with another embodiment of the present invention is illustrated in FIGS. 3A and 3B. In FIG. 3A, control signals are sent to electroactive polymer actuators (not shown) within tubular portions 215a, 215b and 215c, such that chambers A and C (which correspond to the internal volume of tubular portions 215a and 215c) are contracted, while chamber B (which corresponds to the internal volume of tubular portion 215b) is expanded. Due to the directional orientation of check valve 216a in FIG. 3A (which is schematically illustrated as a duckbill check valve), upon contraction of chamber A and expansion of chamber B, fluid flows from chamber A through valve 216a to chamber B as shown. However, the directional orientation of the check valve 216b serves to prevent an analogous current flow from chamber C to chamber B when chamber C is contracted and chamber B is expanded.

Subsequently, as illustrated in FIG. 3B, control signals are provided to expand chambers A and C and to contract chamber B. Due to the directional orientation of the check valve 216*b*, upon contraction of chamber B and expansion of chamber C, fluid flows from chamber B through valve 216*b* to chamber C as shown. However, an analogous current flow does not occur from chamber B to chamber A upon contraction of chamber B and expansion of chamber A, due to the directional orientation of the check valve 216*a*. In this way, a bolus of fluid is advanced from chamber A to chamber B to chamber C.

Because the flow provided by the bypass pumps of the present invention is peristaltic and pulsatile, it can be tailored to mimic the systole and diastole of the heart, and for this reason is believed to have physiological benefits that not obtained with prior art, constant flow bypass pumps. Such physiological benefits would likely increase with increasing bypass duration, for example, as in long-term extracorporeal oxygenation for lung disease.

Pumps designed in accordance with the present invention can have a valve provided at each end of each contactable and expandable tubular portion. Thus, where one tubular portion is selected, two valves may be employed; where two tubular portions are selected, three valves may be employed; and so forth. More generally, where n tubular portions are selected, n+1 valves may be employed, wherein n is an integer of one or more.

In some modes of operation, alternating tubular portions are operated in synchronicity. As a specific example, at a time when the $1^{st}$, $3^{rd}$, $5^{th}$, etc. tubular portions are simultaneously contracted, the $2^{nd}$, $4^{th}$, $6^{th}$, etc. tubular portions can be simultaneously expanded, and vice versa. In general, the odd numbered tubular portions (within a sequence of tubular portions separated by valves) can be operated in a fashion that is out of phase (up to and including 180 degrees out of phase) with the operation of the even numbered tubular portions.

A wide variety of valves, including check valves and control valves, can be used in connection with the present invention.

Check valves are valves that allow fluid to flow in a one direction, while closing to prevent backflow in the opposite direction. Examples include the duckbill check valves described above as well as poppet check valves, umbrella check valves, swing check valves, tilting disk check valves, spring loaded check valves, wafer check valves, leaflet valves and so forth.

Control valves are valves that regulate fluid flow in response to a control signal, for example, using electrical or hydraulic actuators. Control valves are available which use a number of actuated valving elements, for example, ball, cone, sleeve, poppet, rotary spool or sliding spool valving elements. Control valves can also be employed that utilize electroactive polymer actuators to control fluid flow. For example, electroative-polymer-constricted tubing can act as a control valve.

Figure 9A:
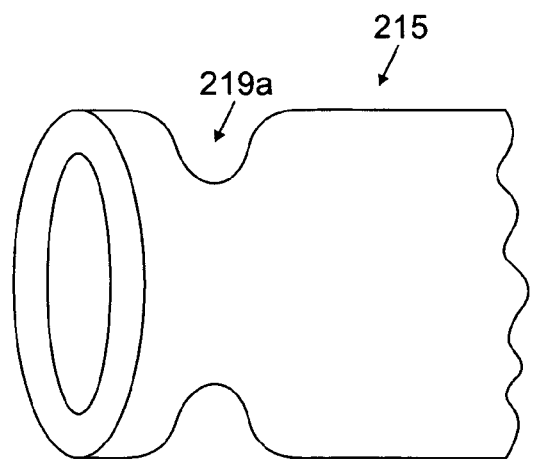
FIGS. 9A-9C are partial, schematic, perspective views illustrating the advancement of a contracted inner volume along the longitudinal length of a tubular portion containing a series of ring shaped electroactive polymer actuators, in accordance with an embodiment of the present invention.
Figure 9B:
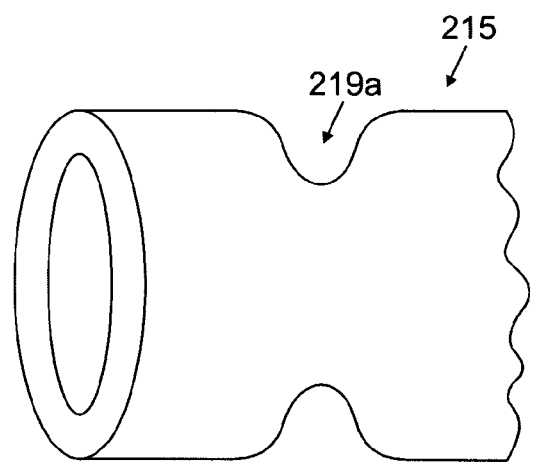
Figure 9C:
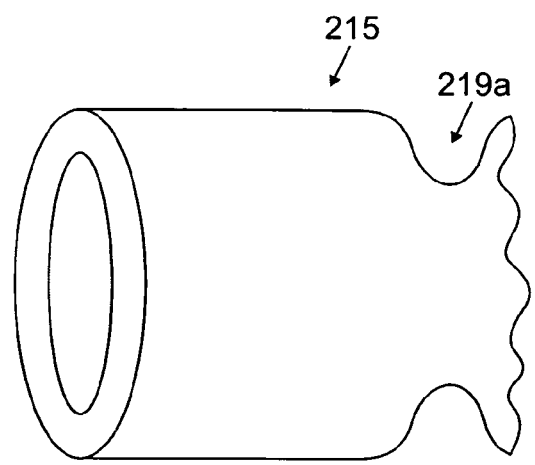

In other embodiments the pump is valveless. Valveless operation can be achieved, for example, by moving a contracted site along the length of the tubular portion. As a specific example, a series of closely spaced circumferentially wrapped electroactive polymer actuators can be provided within a tubular portion. During operation, the actuators can be sequentially contracted, resulting in movement of a contracted site of near-occlusion along the length of the tubular portion. This is illustrated in FIGS. 9A-9C. Referring now to FIG. 9A, a first actuator is activated, resulting in a first contracted region 219*a* within tubular portion 215. Subsequently, another actuator is activated, resulting in a second contracted region 219*b* within tubular portion 215 (see FIG. 9B); followed by activation of yet another actuator resulting in a third contracted region 219*c* within tubular portion 215 (see FIG. 9C). By spacing the actuators sufficiently closely to one another, the overall effect is the advancement of a contracted region along the length of the tubular region. Multiple contracted regions can be concurrently advanced with suitable intervals between the contracted regions, resulting in a pulsed output from the tubular portion.

Similar effects can be achieved, for example, by actuating a series of short segments containing multiple actuators (e.g., a short segment of two helices with counter-opposed wrapping). Similar effects can also be achieved, for example, by a series of closely spaced helices, all having the same helical angle and sense of rotation. This arrangement would result in the apparent advancement of a helical contracted region along the length of the tubular portion.

The precise configuration of the electroactive polymer actuator(s) within the tubular portion(s) of the bypass pumps of the present invention is unimportant so long as the internal volume of the tubular portion can be contracted and expanded as desired upon providing appropriate electrical signals to the electroactive polymer actuators.

Figure 4A:
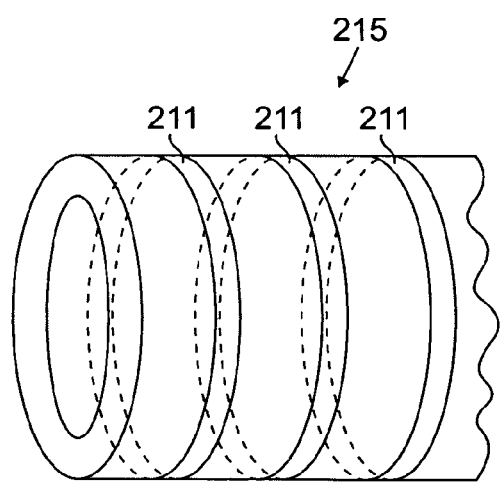
FIGS. 4A-4C are partial, schematic, perspective views illustrating the disposition of electroactive polymer actuators within a tubular portion of a bypass pump in accordance with various embodiments of the present invention.
Figure 4B:
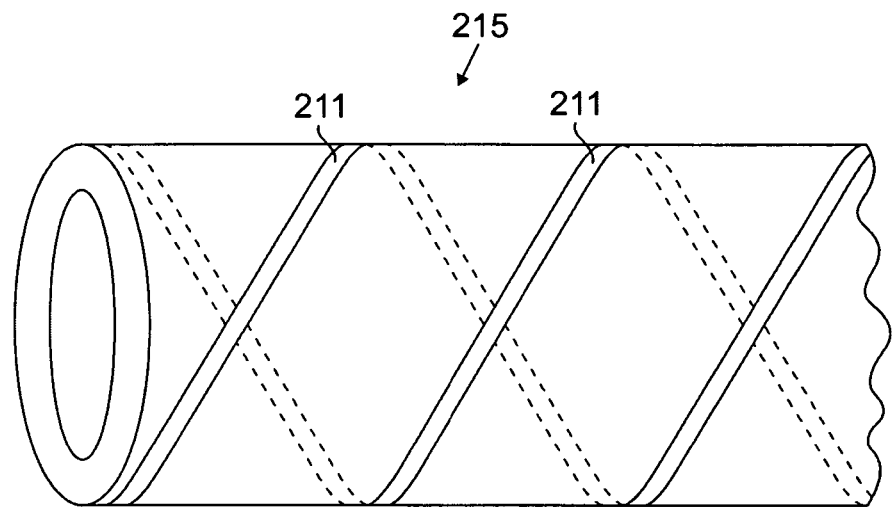
Figure 4C:
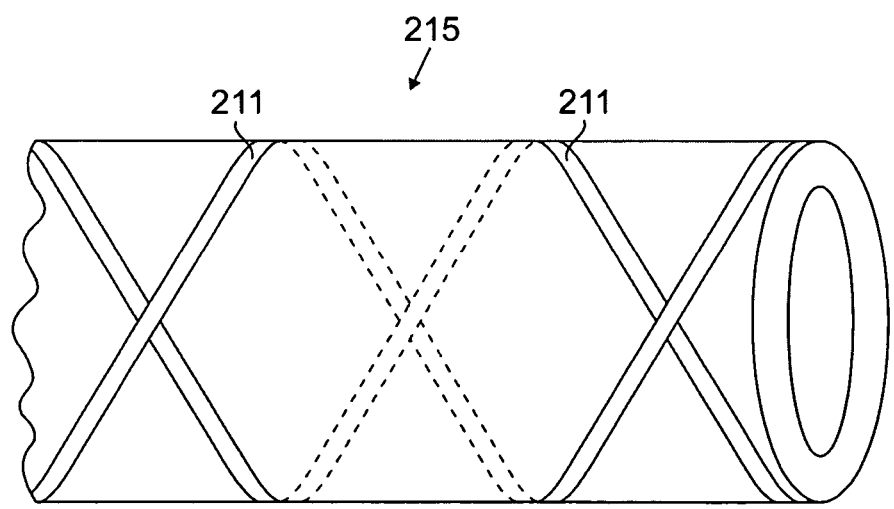

In some embodiments, the electroactive polymer actuators are at least partially wrapped around or integrated within an elastic tubular member. Two particular configurations are illustrated schematically in FIGS. 4A and 4B. In FIG. 4A, electroactive polymer actuators 211 are circumferentially wrapped around a tubular member 215. In FIG. 4B, two electroactive polymer actuators 211 are helically wrapped around a tubular member 215. The two helices 211 have the same sense of rotational direction. As defined herein a "helix" is a curve that is formed by a straight line drawn upon a plane when that plane is wrapped around a cylinder. Helices have helical angles that lie between 0 degrees (i.e., circumferential rotation around the axis of the cylinder, but no advancement along the length of the cylinder) and 90 degrees (i.e., advancement along the length of the cylinder, but no circumferential rotation). In other embodiments, braided electroactive polymer actuators are provided in connection with the tubular portion 215. For example, two helices with opposite senses of rotational direction (see, e.g., the electroactive polymer actuators 211 of FIG. 4C) can be employed to provide a simple braided structure. Other more complex braided structures can also be beneficially employed.

Figure 5A:
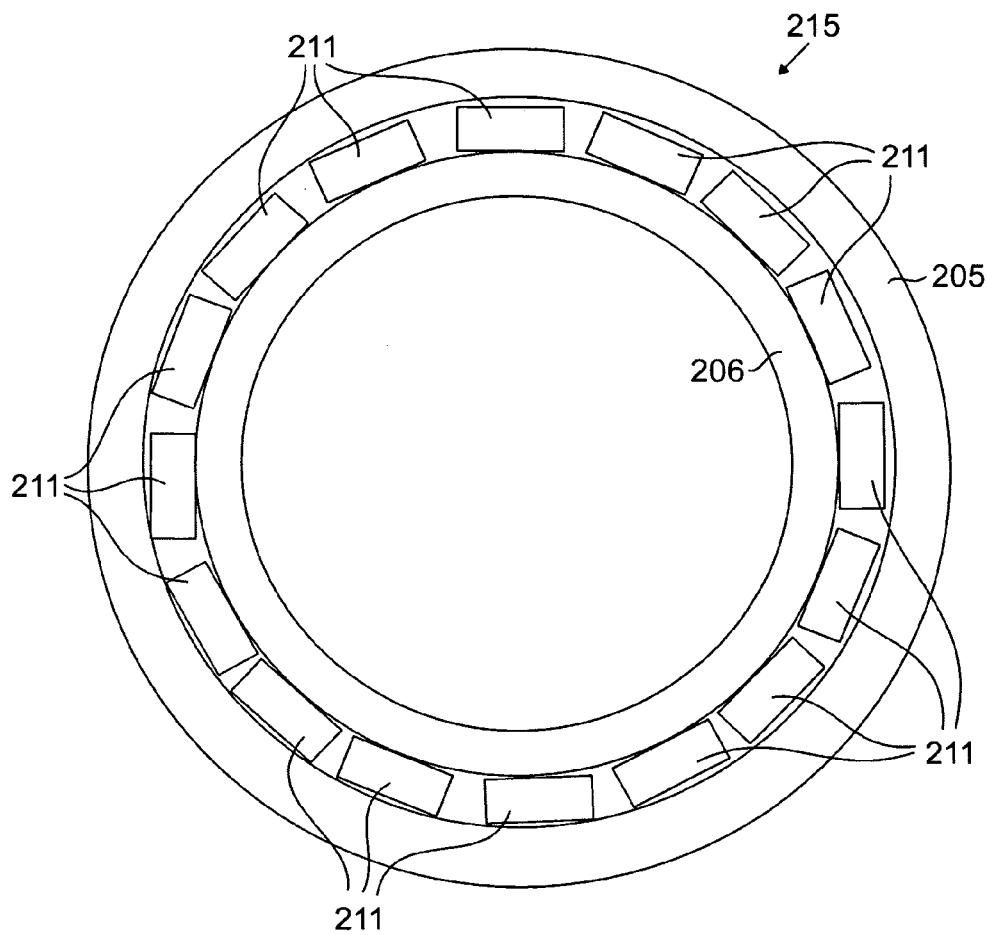
FIG. 5A is a schematic, cross-sectional view of a tubular portion of a bypass pump in accordance with an embodiment of the present invention.

FIG. 5A illustrates a schematic cross-sectional view of a tubular portion 215, in which sixteen electroactive polymer actuators 211 are provided between an outer tubular layer 205 and an inner tubular layer 206. Although not illustrated, the actuators are helically wrapped around the inner tubular layer 205 in this particular embodiment.

The outer and inner layers 205, 206 that are employed can be selected from a number of flexible materials and can be formed from one or more polymeric materials. Polymeric materials useful in the construction of the outer and inner layers 205, 206 include the following: polyolefins such as metallocene catalyzed polyethylenes, polypropylenes, and polybutylenes and copolymers thereof; ethylenic polymers such as polystyrene; ethylenic copolymers such as ethylene vinyl acetate (EVA), butadiene-styrene copolymers and copolymers of ethylene with acrylic acid or methacrylic acid; polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers such as polyether block amides; polyethers; elastomers such as elastomeric polyurethanes and polyurethane copolymers; silicones; polycarbonates; polychloroprene; nitrile rubber; butyl rubber; polysulfide rubber; cis-1,4-polyisoprene; ethylene propylene terpolymers; as well as mixtures and block or random copolymers of any of the foregoing are examples of polymers useful for manufacturing the medical devices of the present invention. Elastomeric polymeric materials can be used for the construction of the outer and inner layers 205, 206.

As a specific example, the outer and inner layers 205, 206 can comprise urethane or silicone polymers. An inner coating for compatible blood contact (not illustrated) may also be provided on an inner surface of inner layer 206 as is known in the art, if desired.

Numerous design choices are available for the electroactive polymer actuators that are used in the pumps of the present invention. As an example, the electroactive polymer actuators (e.g., the electroactive polymer actuators 211 of FIGS. 4A, 4B and 5A) can be of a design like that discussed above in connection with FIG. 1 which, as previously discussed, includes an active member 12 (which is illustrated in the form of a cylinder in FIG. 1), electrolyte 14 and a counter-electrode 18 (which is illustrated in the form of a coil in FIG. 1).

Figure 5B:
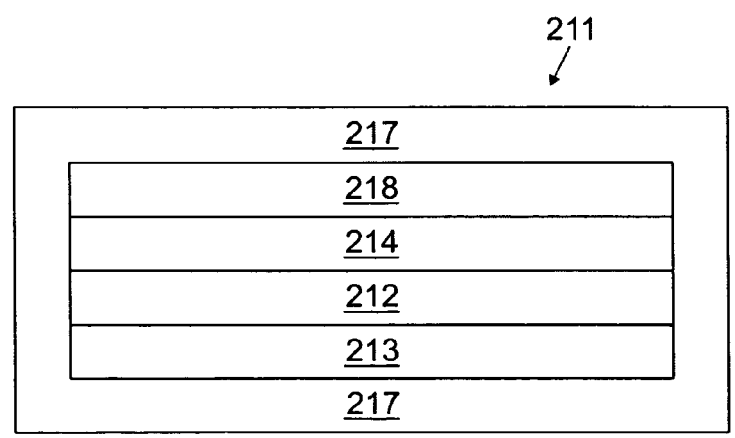
FIG. 5B is a schematic cross-sectional view of an electroactive polymer actuator, in accordance with an embodiment of the present invention.

Another electroactive polymer actuator 211 design is schematically illustrated in cross-section in FIG. 5B. As seen in this figure, the internal elements of the actuator 211 are surrounded by a barrier region 217, which can be an elastomeric non-reactive material selected, for example, from the list of polymer materials provided above.

The actuator includes an active region 212, which comprises an electroactive polymer as previously discussed. Polypyrrole, polysulfone, polyacetylene and polyaniline are specific examples of electroactive polymers. In the embodiment illustrated, the active region 212 is further provided with a conductive electrical contact 213 to enhance electrical contact with the control unit. The conductive electrical contact 213 may be formed from any suitable electrical conductor, for example, a metal such as gold or platinum. The conductive electrical contact 213 can be, for example, in wire or film form and can be applied, for example, by electroplating, chemical deposition, or printing.

A counter-electrode 218 is also included. As above, the counter-electrode 218 can be formed from any suitable electrical conductor, for example, a metal such as gold or platinum. The counter-electrode 118 can be, for example, in wire or film form and can be applied, for example, by electroplating, chemical deposition, or printing.

An electrolyte-containing region 214 is provided adjacent the active region 212 and the counter-electrode 218, and can be, for example, a liquid, a gel, or a solid electrolyte layer, as discussed above. It is beneficial that the active region 212 avoid contact with the counter-electrode 218 to prevent short-circuiting. The characteristics of the electrolyte that is selected may inherently prevent such contact from occurring, particularly in the case of a solid electrolyte. If not, for example, where a liquid or non-robust gel is used as an electrolyte, additional measures may be taken to keep the active region 212 from contacting the counter-electrode 218. For example, a series of insulating material spacers with interstitial electrolyte can be placed between the active region 212 and the counter-electrode 218. Similarly, electrolyte may be provided within pores or perforations of an insulating material layer or within the interstices of a woven layer or mesh of insulating material to prevent short-circuiting. Suitable insulating materials include insulating polymers, including those listed above. PTFE is one specific example.

Layered structures like that illustrated in FIG. 5B are efficient from a manufacturing perspective and can be formed by numerous techniques. For example, a layer of barrier material 217 can be provided, after which layers of material corresponding to the active region contact 213, the active region 212, the electrolyte-containing region 214 and the counter-electrode 218, respectively, are applied. Finally, an additional layer of layer of barrier material 217 is provided over the entire structure to provide the structure of FIG. 5B.

In another example, a first composite stack is formed by depositing, on a first layer barrier material 217, layers of material that correspond to the active region contact 213 and the active region 212. At the same time, a second composite stack is formed depositing a layer of material corresponding to the counter-electrode 218 on a second layer of barrier material 217. An electrolyte-containing layer 214 is then laminated between the first and second composite stacks to provide the structure of FIG. 5B.

Myriad configurations are possible. Referring again to FIG. 5A, in another embodiment, the various elements of the electroactive polymer actuators (e.g., counter-electrode, electrolyte-containing region, active region, as well as an active region contact, if desired) can be applied to a substrate sheet that corresponds to outer layer 205. This structure is subsequently wrapped around inner layer 206 to form the tubular portion shown.

In yet another embodiment, layers of material that correspond to the active region contact, if desired, and the active region are deposited on a substrate sheet corresponding to outer layer 206. A layer of material corresponding to the counter-electrode is deposited on a substrate sheet corresponding to inner layer 205. An electrolyte-containing layer is then laminated between these sheets, and the resulting composite structure rolled into the shape of tube.

These latter embodiments allow interconnect wiring to be deposited on the substrate sheets, simplifying electrical connection between the various electroactive polymer actuators.

During operation, a control unit can be used to apply an appropriate potential between the active regions and the counter-electrode layers of the actuators. In general, by applying a sufficient potential difference of a first polarity, the electroactive polymer active regions will contract, decreasing the internal volume of the tubular portion. By applying a sufficient potential difference having an opposite polarity, on the other hand, the electroactive polymer active regions will expand, increasing the internal volume of the tubular portion.

In some embodiments of the invention (e.g., the embodiments having n tubular portions and n+1 valves discussed above), all of the active layers within a given tubular portion may be shorted to one another, as can all of the counter-electrode layers, allowing all of the actuators within that particular tubular portion to simultaneously expand and contract. Where multiple (i.e., three or more) tubular portions are utilized, it may be desirable to short together all of the active layers (and counter-electrode layers) within alternating tubular portions, allowing the actuators within the alternating tubular portions to simultaneously expand and contract.

Strain gauges can be employed to provide electronic feedback concerning the degree of contraction of the tubular portion(s) of the bypass pump. This electronic feedback will also provide a number of additional advantages, including closed-loop feedback control based on pressure, compensation for physiologic changes, greater stability, error correction, and immunity from drift. Strain gauges suitable for use in the present invention include (a) feedback electroactive polymer elements whose impedance or resistance varies as a function of the amount of strain in the device, (b) linear displacement transducers (e.g., an iron slug slidably positioned in the core of a coil) and (c) conventional strain gauges in which the resistance of the device varies as a function of the amount of strain in the device, thus allowing the amount of strain to be readily quantified and monitored. Such strain gauges are commercially available from a number of different sources, including National Instruments Co., Austin, Tex., and include piezoresistive strain gauges (for which resistance varies nonlinearly with strain) and bonded metallic strain gauges (for which resistance typically varies linearly with strain).

The bypass pumps of the present invention can be used in essentially any medical procedure in which circulatory support of a patient is desired. Many bypass circuit arrangements are known in the art and are selected, for example, depending upon the preference of the attending physician and the particular procedure that is performed. For instance, although a venous cannula (or catheter) is placed in the femoral vein in the example to follow, it can also be placed, for example, in the right atrium, the superior/inferior vena cava, or the left atrium (e.g., for a left ventricle-aortal bypass, using the patient's lungs from oxygenation). Similarly, although an arterial cannula (or catheter) is placed in the femoral artery in the example to follow, it can also be placed, for example, in the ascending aorta or in the pulmonary artery (e.g., for right heart bypass, using the patient's lungs from oxygenation).

Figure 6:
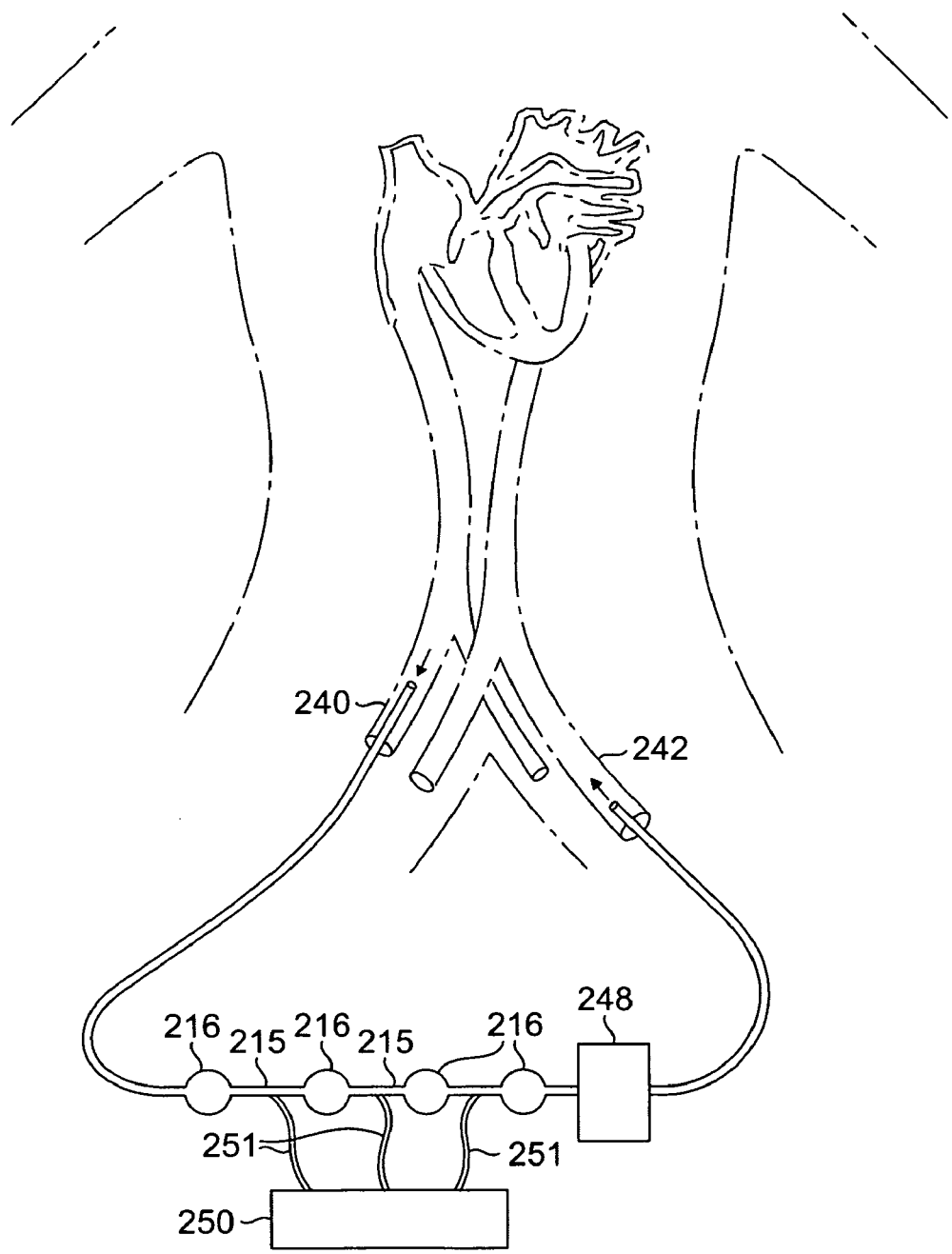
FIG. 6 is a schematic view of a bypass procedure utilizing a bypass pump apparatus in accordance with an embodiment of the present invention.

A specific bypass circuit (specifically, a femoral-femoral bypass circuit) can be provided as illustrated in FIG. 6 wherein a femoral venous cannula allows blood to be withdrawn via a femoral vein 240. A femoral arterial cannula allows the return of blood to the femoral artery 242 to achieve femoral-femoral total extracorporeal circulation. Control signals are provided to actuators in the tubular portions 215 via control cables 251 from control unit 250 to provide flow as previously described.

The bypass circuit illustrated further includes an oxygenator 248. Oxygenators are well known in the art. Two common types of oxygenators are bubble oxygenators and membrane oxygenators. With bubble oxygenators, gas bubbles containing oxygen are introduced directly into the blood. Usually, a defoamer is employed to remove gas bubbles from the blood following bubble oxygenation. Examples of bubble oxygenators are disclosed in U.S. Pat. Nos. 4,374,088 and 4,637,917, the disclosures of which are hereby incorporated by reference. With membrane oxygenators, oxygen passes along one side of a permeable membrane and blood along the other. The permeable membrane has a sufficient pore size such that oxygen molecules pass through the membrane to be diffused into the blood as dissolved oxygen. However, the pores are sufficiently small such that blood cannot flow to the oxygen side. Examples of the use of a microporous membrane sheet to oxygenate blood where blood flows along one side of a membrane sheet and oxygen along the other are disclosed in U.S. Pat. Nos. 4,451,562 and 4,424,190, the disclosures of which are hereby incorporated by reference. Bundles of hollow fiber membrane tubes may also be used, where oxygen passes through the hollows of the tubes and blood flows along the outside of the tubes. Hollow tube membrane oxygenators are disclosed in U.S. Pat. Nos. 4,948,560, Re. 33,932, U.S. Pat. Nos. 4,639,353, and 6,001,306, the disclosures of which are hereby incorporated by reference.

The bypass pumps of the present invention can be provided with modular fittings or quick-connects to facilitate connections with arterial or venous cannulas or catheters, Moreover, embolic protection filters, as well as various additional art-known bypass pump accessories, can be employed in connection with the bypass pumps of the present invention.

The waveform of the control signals sent from the control unit to the electroactive polymer actuators can be based on a wide variety of criteria. For example, the control signals can simply consist of one or more simple sinusoidal or square waveforms of predetermined frequency and amplitude. Alternatively, the control signal can be provided based on a look-up table that is stored to the memory of a computer. The waveform of the control signals can also be regulated based on feedback from one or more physiological sensor inputs over time, including arterial pressure or flow, venous pressure or flow, $pO_2$, pH, $pCO_2$, EKG, and so forth. For instance, the waveform of the control signals can be determined from a look-up table, based on input from one or more of the above physiological sensors.

Numerous control unit configurations are readily available in the electronics art. For example, control signals can be generated using one or more function/pulse generators as a control unit. As another example, control signals can be generated by computer (e.g., a personal computer equipped with an electronic interface and drivers), based on stored program, which can take into account inputs from physiological sensors as discussed above. Additional control unit configurations will become readily apparent to those of ordinary skill in the art.

In some embodiments of the present invention, the size of the control unit can be reduced by sending control data (e.g., waveform data) over a wireless communications interface. Inexpensive wireless interfaces are presently available from a number of sources, including Bluetooth™ wireless interfaces available from Motorola and IEEE 802.5B wireless interfaces available, for example, from Cisco, Apple and Lucent. For example, a wireless interface associated with a remote computer (e.g., a computer placed elsewhere in the operating room) can send waveform data to a companion wireless interface, which constitutes part of the pump apparatus. The received waveform data can then be routed to drivers, which power the actuators within the pump.

Figure 7:
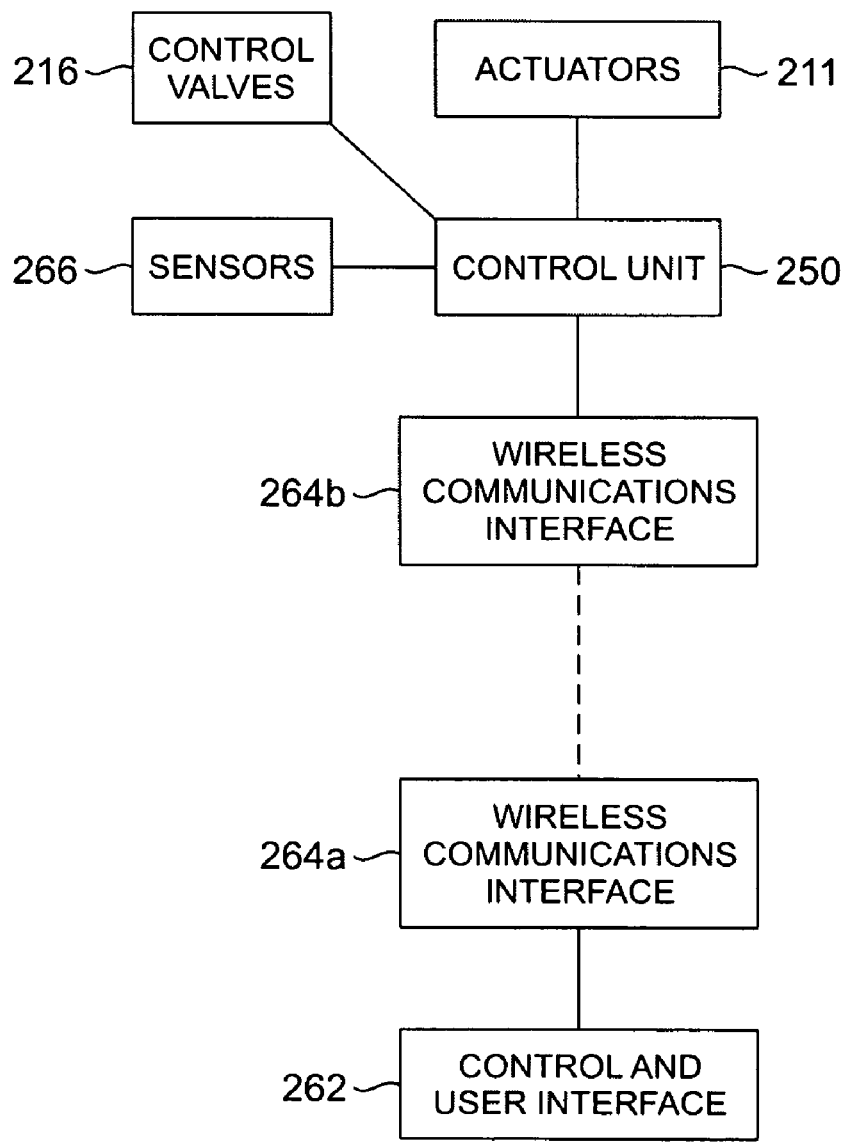
FIG. 7 depicts an exemplary bypass pump in block diagram format in accordance with another embodiment of the present invention.

FIG. 7 is a simplified electrical schematic diagram of a bypass pump apparatus in accordance with an embodiment of the present invention. As previously discussed, the bypass pump contains one or more electroactive polymer actuators 211. The pump illustrated in FIG. 7 also includes one or more control valves 216 and one or more sensors 266 (e.g., strain gauges and/or physiological sensors). A control unit 250, for example a computer equipped with an electronic interface and drivers: (a) provides an appropriate signal or signals to expand and contract the actuators 211, (b) provides an appropriate signal or signals to open or close the control valve as required, and (c) collects information from the sensors 266 (e.g., by measuring the impedance, voltage, etc. associated with the sensors 266). Control unit 150 is also provided with a source of power. Depending on the procedure time and/or the volume of the blood to be moved, a battery can be used as a source for power. Such power sources have utility, for example, in emergency field surgery and bridge to surgery applications.

Control of the pump in FIG. 7 is implemented remotely via a computer, which as is typical, contains components for control and user interface 262. Data is exchanged with the control unit 250 of the bypass pump via a wireless communication interface. Wireless interface 164a, which is associated with the control and user interface 262, communicates with a remote companion wireless interface 164b, which is associated with the control unit 250.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A pump apparatus comprising:
   (a) a tubular member comprising an electroactive polymer actuator that is configured to expand and contract at least a portion of an inner volume of said tubular member based upon received control signals; and
   (b) a control unit electrically coupled to said actuator and sending said control signals to said actuator.

2. The pump apparatus of claim 1, further comprising a valve in fluid communication with said inner volume of said tubular member.

3. The pump apparatus of claim 2, wherein said valve is a control valve.

4. The pump apparatus of claim 2, wherein said valve is a check valve.

5. The pump apparatus of claim 1, further comprising first and second valves in fluid communication with said inner volume of said tubular member, wherein said first valve is disposed between said tubular member and an inlet of said pump apparatus and wherein said second valve is disposed between said tubular member and an outlet of said pump apparatus.

6. The pump apparatus of claim 5, wherein said first valve is configured to allow increased fluid flow when said inner volume is expanded and decreased fluid flow when said inner volume is contracted, and wherein said second valve is configured to allow increased fluid flow when said inner volume is contracted and decreased fluid flow when said inner volume is expanded.

7. The pump apparatus of claim 1, wherein said tubular member comprises a plurality of electroactive polymer actuators that are configured to expand and contract said at least a portion of said inner volume of said tubular member based upon said control signals.

8. The pump apparatus of claim 7, wherein said electroactive polymer actuators and said control signals are configured to advance a region of contracted inner volume along the longitudinal length of the tubular member.

9. The pump apparatus of claim 1, wherein said electroactive polymer actuator at least partially wraps round a longitudinal axis of said tubular member.

10. The pump apparatus of claim 9, wherein said electroactive polymer actuator circumferentially wraps around said tubular member longitudinal axis.

11. The pump apparatus of claim 9, wherein said electroactive polymer actuator helically wraps around said tubular member longitudinal axis.

12. The pump apparatus of claim 1, wherein said pump apparatus comprises a plurality of tubular members.

13. The pump apparatus of claim 12, wherein said pump apparatus comprises n tubular members and n+1 valves, where n is an integer greater than or equal to 1.

14. The pump apparatus of claim 1, wherein said electroactive polymer actuator comprises an electroactive polymer region, a counter-electrode region, and an electrolyte-containing region disposed between said electroactive polymer region and said counter-electrode region.

15. The pump apparatus of claim 14, wherein said electroactive polymer region comprises an electroactive polymer selected from polyaniline, polypyrrole, polysulfone, and polyacetylene.

16. The pump apparatus of claim 1, wherein said electroactive polymer actuator is disposed between inner and outer walls of said tubular member.

17. The pump apparatus of claim 16, wherein said tubular member comprises an inner layer, an outer layer, a counter-electrode region, an electrolyte containing region and a electroactive polymer region, and wherein said counter-electrode region, said electrolyte containing region and said electroactive polymer region are disposed between said inner and outer layers.

18. The pump apparatus of claim 1, wherein said control unit comprises a pulse generator.

19. The pump apparatus of claim 1, wherein said control unit comprises a computer.

20. The pump apparatus of claim 1, further comprising a wireless transceiver coupled to said control unit.

21. The pump apparatus of claim 1, further comprising a sensor coupled to said control unit.

22. The pump apparatus of claim 21, wherein said sensor is a strain gauge.

23. The pump apparatus of claim 21, wherein said sensor is a chemical sensor that measures a detectable chemical species.

24. The pump apparatus of claim 1, wherein said pump apparatus is a bypass pump apparatus.

25. A method of providing circulatory support for a patent comprising:
   providing the bypass pump apparatus of claim 24;
   placing an inlet of said pump apparatus in fluid communication with the venous side of said patient's vascular system;
   placing an outlet of said pump apparatus in fluid communication with the arterial side of said patient's vascular system; and
   sending said control signals to said electroactive polymer actuator thereby pumping blood from the venous side to the arterial side of said patient's vascular system.

26. The method of claim 25, wherein said pump apparatus comprises a series of electroactive polymer actuators, and wherein said control signals sequentially actuate said series of electroactive polymer actuators such that a region of contracted inner volume is advanced along the longitudinal length of the tubular member.

27. The method of claim 25, wherein said control signals comprise a wave having a predetermined frequency and amplitude.

28. The method of claim 27, wherein the frequency, the amplitude, or both the frequency and amplitude of the wave are manually set by a human operator.

29. The method of claim 27, wherein the form of the wave is determined by a computer.

30. The method of claim 27, wherein the form of the wave is determined by a computer based on a patient sensor input.

31. The pump apparatus of claim 1, wherein said control unit comprises a battery.

32. The pump apparatus of claim 1, wherein said electroactive polymer actuator is configured to expand and contract said inner volume of said tubular member by contraction and expansion of the tube walls, based upon said received control signals.

* * * * *

UNITED STATES PATENT AND TRADEMARK OFFICE
CERTIFICATE OF CORRECTION

PATENT NO. : 7,371,223 B2
APPLICATION NO. : 10/262817
DATED : May 13, 2008
INVENTOR(S) : Couvillon, Jr. et al.

It is certified that error appears in the above-identified patent and that said Letters Patent is hereby corrected as shown below:

Abstract, line 11, after "for", insert --a--.

References Cited, Other Publications, Col. 2, line 14, after "Muscles)", change "Newlsetter" to --Newsletter--.

References Cited, Other Publications, Col. 2, line 15, after "modeling", change "an" to --and--.

Specification, Col. 1, line 22, after "Unfortunately,", change "roller type" to --roller-type--.

Specification, Col. 1, line 36, after first word "Many", change "or" to --of--.

Specification, Col. 2, line 8, after "where", insert --n--.

Specification, Col. 2, line 15, after "(e.g.", insert --,--.

Specification, Col. 2, line 24, after "between", delete "and".

Specification, Col. 3, line 2, before "roller", delete first words "prior art".

Specification, Col. 3, line 12, after "pump", delete ",".

Specification, Col. 5, line 33, after "Stretching:", change "Counter-on" to --Counter-ion--.

Specification, Col. 5, line 48, after "occurs", change "in vivo" to --*in vivo*--.

Specification, Col. 6, line 42, after "left to", insert --right--.

Specification, Col. 6, line 48, after "will be", delete --will be--.

UNITED STATES PATENT AND TRADEMARK OFFICE
CERTIFICATE OF CORRECTION

PATENT NO. : 7,371,223 B2
APPLICATION NO. : 10/262817
DATED : May 13, 2008
INVENTOR(S) : Couvillon, Jr. et al.

It is certified that error appears in the above-identified patent and that said Letters Patent is hereby corrected as shown below:

Specification, Col. 7, line 14, before first words "not obtained", insert --are-- and after "prior art", delete ",".

Specification, Col. 7, line 53, after first word "example,", change "electroative-polymer-constricted" to --electroactive-polymer-constricted--.

Specification, Col. 10, line 8, after "layer of", delete "layer of".

Claim 17, Col. 14, line 6, after "an", change "electrolyte containing" to --electrolyte-containing-- and after "and", change last word "a" to --an--.

Claim 17, Col. 14, line 8, after "said", change "electrolyte containing" to --electrolyte-containing--.

Claim 25, Col. 14, line 28, after "for a", change last word "patent" to --patient--.

Signed and Sealed this

Nineteenth Day of May, 2009

JOHN DOLL
*Acting Director of the United States Patent and Trademark Office*